United States Patent
Trah et al.

(10) Patent No.: US 6,953,811 B2
(45) Date of Patent: Oct. 11, 2005

(54) N-SUBSTITUTED TETRAHYDROPYRIDINES AND THEIR USE AS PESTICIDES

(75) Inventors: Stephan Trah, Basel (CH); Josef Ehrenfreund, Basel (CH); Peter Maienfisch, Basel (CH); André Jeanguenat, Basel (CH); Saleem Farooq, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 15 days.

(21) Appl. No.: 10/470,790

(22) PCT Filed: Feb. 4, 2002

(86) PCT No.: PCT/EP02/01129

§ 371 (c)(1),
(2), (4) Date: Jul. 30, 2003

(87) PCT Pub. No.: WO02/068392

PCT Pub. Date: Sep. 6, 2002

(65) Prior Publication Data

US 2004/0102487 A1 May 27, 2004

(30) Foreign Application Priority Data

Feb. 5, 2001 (CH) ................................................ 0198/01

(51) Int. Cl.[7] ........................ A01N 43/40; C07D 211/70; C07D 211/94
(52) U.S. Cl. ........................ 514/357; 514/358; 546/330; 546/333
(58) Field of Search ................................ 514/357, 358; 546/330, 333

(56) References Cited

U.S. PATENT DOCUMENTS 6,017,931 A  1/2000 Silverman et al.

FOREIGN PATENT DOCUMENTS

WO  98 22438  5/1998
WO  01 17964  3/2001

*Primary Examiner*—Patricia L. Morris
(74) *Attorney, Agent, or Firm*—Jacqueline Haley

(57) ABSTRACT

A description is given of compounds of the formula

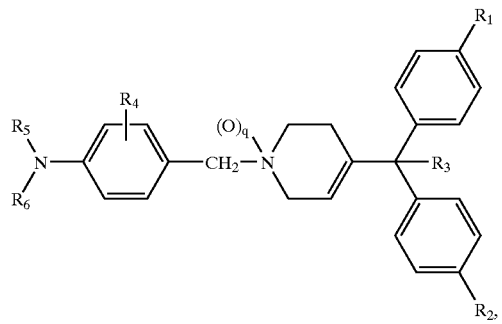

(I)

in which $R_1$ and $R_2$ independently of one another are halogen, $C_1-C_6$alkyl, halo-$C_1-C_6$alkyl, $C_1-C_6$alkoxy, halo-$C_1-C_6$alkoxy, or $SF_5$, $R_3$ is hydrogen, OH, halogen, $C_1-C_6$alkoxy or —O—C(=O)—$C_1-C_6$alkyl, $R_4$ is for example hydrogen, halogen, $C_1-C_6$alkyl, halo-$C_1-C_6$alkyl, $C_1-C_6$alkoxy, halo-$C_1-C_6$alkoxy or SCN;

$R_5$ and $R_6$ independently of one another are for example hydrogen, $C_1-C_{12}$alkyl, halo-$C_1-C_{12}$alkyl, $C_2-C_{12}$alkenyl, halo-$C_2-C_{12}$alkenyl or $C_2-C_{12}$alkynyl; and q is 0 or 1;

and, where appropriate, E/Z isomers, E/Z isomer mixtures and/or tautomers, each in free form or in salt form; a process for the preparation of these compounds and their use, pesticide compositions whose active ingredient is selected from these compounds, or an agrochemically useable salt thereof, a process for preparing these compositions, and their use, plant propagation material treated with these compositions, and a method of combating pests.

5 Claims, No Drawings

N-SUBSTITUTED TETRAHYDROPYRIDINES AND THEIR USE AS PESTICIDES

This application is a 371 filing of International Application No. PCT/EP02/01129, filed Feb. 4, 2002, the contents of which are incorporated herein by reference.

The present invention provides
(1) a compound of the formula

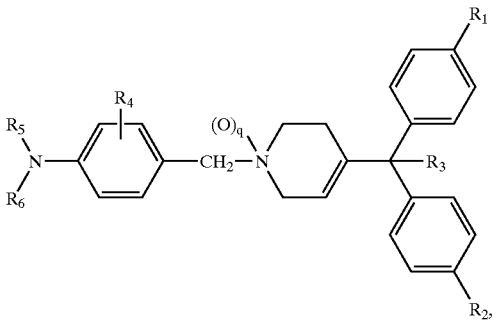

(I)

in which $R_1$ and $R_2$ independently of one another are halogen, $C_1$–$C_6$alkyl, halo-$C_1$–$C_6$alkyl, $C_1$–$C_6$alkoxy, halo-$C_1$–$C_6$alkoxy, —S(=O)$_p$—$R_9$ or SF$_5$, $R_3$ is hydrogen, OH, halogen, $C_1$–$C_6$alkoxy or —O—C(=O)—$C_1$–$C_6$alkyl, $R_4$ is hydrogen, halogen, $C_1$–$C_6$alkyl, halo-$C_1$–$C_6$alkyl, $C_1$–$C_6$alkoxy, halo-$C_1$–$C_6$alkoxy, —S(=O)$_p$—$R_9$ or SCN;

$R_5$ and $R_6$ independently of one another are hydrogen, $C_1$–$C_{12}$alkyl, halo-$C_1$–$C_{12}$alkyl, $C_2$–$C_{12}$alkenyl, halo-$C_2$–$C_{12}$alkenyl, $C_2$–$C_{12}$alkynyl, halo-$C_2$–$C_{12}$alkynyl, $C_3$–$C_8$cycloalkyl, —C(=O)—O—$R_7$, —C(=S)—O—$R_8$, —C(=Y)—Z—$R_8$, —S(=O)$_p$—$R_9$, aryl, aryl-$C_1$–$C_6$alkyl, heterocyclyl or heterocyclyl-$C_1$–$C_6$alkyl; or, depending on substitution possibilities on the ring are $C_3$–$C_8$cycloalkyl, aryl, aryl-$C_1$–$C_6$alkyl, heterocyclyl or heterocyclyl-$C_1$–$C_6$alkyl, substituted from one to five times independently of one another by halogen, hydroxyl, cyano, nitro, $C_1$–$C_6$alkyl, halo-$C_1$–$C_6$alkyl, $C_1$–$C_6$alkoxy or halo-$C_1$–$C_6$alkoxy; or in common, together with the nitrogen atom to which they are attached, form a heterocyclic ring which is unsubstituted or substituted;

Y is oxygen or sulfur;

Z is a bond, —NR$_{10}$— or sulfur;

$R_7$ is $C_1$–$C_6$alkoxy-$C_1$–$C_6$alkyl, $C_1$–$C_6$alkylthio-$C_1$–$C_6$alkyl, $C_1$–$C_6$alkylamino-$C_1$–$C_6$alkyl, $C_3$–$C_6$alkynyl, $C_1$–$C_6$alkyl-S(=O)$_p$—$C_1$–$C_6$alkyl, $C_3$–$C_8$cycloalkyl, aryl, aryl-$C_1$–$C_6$alkyl, heterocyclyl or heterocyclyl-$C_1$–$C_6$alkyl; or, depending on substitution possibilities on the ring is $C_3$–$C_8$cycloalkyl, aryl, aryl-$C_1$–$C_6$alkyl, heterocyclyl or heterocyclyl-$C_1$–$C_6$alkyl, substituted from one to five times independently of one another by halogen, cyano, nitro, $C_1$–$C_6$alkyl, halo-$C_1$–$C_6$alkyl, $C_1$–$C_6$alkoxy or halo-$C_1$–$C_6$alkoxy;

$R_8$ is $C_1$–$C_6$alkyl, halo-$C_1$–$C_6$alkyl, $C_1$–$C_6$alkoxy-$C_1$–$C_6$alkyl, $C_1$–$C_6$alkylthio-$C_1$–$C_6$alkyl, $C_2$–$C_6$alkenyl, $C_3$–$C_6$alkynyl, $C_1$–$C_6$alkyl-S(=O)$_p$—$C_1$–$C_6$alkyl, $C_3$–$C_8$cycloalkyl, aryl, aryl-$C_1$–$C_6$alkyl, heterocyclyl or heterocyclyl-$C_1$–$C_6$alkyl; or, depending on substitution possibilities on the ring, is $C_3$–$C_8$cycloalkyl, aryl, aryl-$C_1$–$C_6$alkyl, heterocyclyl or heterocyclyl-$C_1$–$C_6$alkyl substituted from one to five times independently of one another by halogen, cyano, nitro, $C_1$–$C_6$alkyl, halo-$C_1$–$C_6$alkyl, $C_1$–$C_6$alkoxy or halo-$C_1$–$C_6$alkoxy;

$R_9$ is $C_1$–$C_6$alkyl, $C_3$–$C_8$cycloalkyl, halo-$C_1$–$C_6$alkyl or benzyl;

$R_{10}$ is hydrogen, $C_1$–$C_6$alkyl, $C_3$–$C_8$cycloalkyl, halo-$C_1$–$C_6$alkyl or benzyl;

p is 0, 1 or 2; and q is 0 or 1;

and, where appropriate, E/Z isomers, E/Z isomer mixtures and/or tautomers, each in free form or in salt form;

a process for the preparation of these compounds and their use, pesticide compositions whose active ingredient is selected from these compounds, or an agrochemically useable salt thereof, a process and intermediates for preparing these compositions, and their use, plant propagation material treated with these compositions, and a method of combating pests.

The literature proposes certain piperidine derivatives as active ingredients in pesticide compositions. The biological properties of these known compounds are, however, unable to provide full satisfaction in the field of pest control, and so there is a need to provide further compounds having pesticidal properties, particularly for the control of insects and representatives of the order Acarina, this object being achieved in accordance with the invention through the provision of the present compounds of the formula (I).

The compounds of the formula (I) and, where appropriate, their tautomers may form salts, e.g. acid addition salts. These salts are formed, for example, with strong inorganic acids, such as mineral acids, e.g. sulfuric acid, a phosphoric acid or a hydrohalic acid, with strong organic carboxylic acids, such as $C_1$–$C_4$alkanecarboxylic acids, unsubstituted or substituted, for example by halogen, e.g. acetic acid, such as saturated or unsaturated dicarboxylic acids, e.g. oxalic, malonic, maleic, fumaric or phthalic acid, such as hydroxycarboxylic acids, e.g. ascorbic, lactic, malic, tartaric or citric acid, or such as benzoic acid, or with organic sulfonic acids, such as $C_1$–$C_4$alkanesulfonic or arylsulfonic acids, unsubstituted or substituted, for example by halogen, e.g. methanesulfonic or p-toluenesulfonic acid. Furthermore, compounds of the formula (I) containing at least on acidic group may form salts with bases. Suitable salts with bases are, for example, metal salts, such as alkali metal or alkaline earth metal salts, e.g. sodium, potassium or magnesium salts, or salts with ammonia or with an organic amine, such as morpholine, piperidine, pyrrolidine, a mono-, di- or tri-lower alkylamine, e.g. ethyl-, diethyl-, triethyl- or dimethylpropylamine, or a mono-, di- or trihydroxy-lower alkylamine, e.g. mono-, di- or triethanolamine. Furthermore, corresponding inner salts may be formed where appropriate. Preference is given on the one hand to the free form. Among the salts of compounds of the formula (I), the agrochemically advantageous salts are preferred. Above and below, references to the free compounds of the formula (I) and/or their salts should also be understood where appropriate as referring to the corresponding salts, and, conversely, references to the salts should be understood to include the free compounds of the formula (I). Similar comments apply to tautomers of compounds of the formula (I) and their salts.

The general terms used above and below, unless differently defined, have the meanings set out below.

Halogen (halo), as a group per se and also as a structural element of other groups and compounds, such as of haloalkyl, halocycloalkyl, haloalkenyl, haloalkynyl and haloalkoxy, is fluorine, chlorine, bromine or iodine, especially fluorine, chlorine or bromine, but particularly fluorine or chlorine, especially chlorine.

Carbon-containing groups and compounds contain, unless differently defined, in each case from 1 up to and including 20, preferably from 1 up to and including 18, in particular from 1 up to and including 10, especially from 1 up to and including 6, in particular from 1 up to and including 4, especially from 1 up to and including 3, in particular 1 or 2, carbon atoms; methyl is very particularly preferred.

Alkyl, as a group per se and also as a structural element of other groups and compounds, such as, for example, of haloalkyl, alkoxy, alkoxyalkyl, haloalkoxy, alkoxycarbonyl, alkylthio, haloalkylthio, alkylsulfonyl and alkylsulfonyloxy, in each case with appropriate account being taken of the particular number of carbon atoms present in the corresponding group or compound, is either straight-chain, e.g. methyl, ethyl, n-propyl, n-butyl, n-hexyl, n-octyl, n-decyl, n-dodecyl, n-hexadecyl or n-octadecyl, or branched, e.g. isopropyl, isobutyl, sec-butyl, tert-butyl, isopentyl, neopentyl or isohexyl.

Alkenyl and alkynyl, as groups per se and also as structural elements of other groups and compounds, such as of haloalkenyl, haloalkynyl, alkenyloxy, haloalkenyloxy, alkynyloxy or haloalkynyloxy, are straight-chain or branched and contain in each case two or preferably one unsaturated carbon-carbon bond(s). By way of example, mention may be made of vinyl, prop-2-en-1-yl, 2-methylprop-2-en-1-yl, but-2-en-1-yl, but-3-en-1-yl, prop-2-yn-1-yl, but-2-yn-1-yl and but-3-yn-1-yl.

Cycloalkyl, as a group per se and also as a structural element of other groups and compounds, such as, for example, of alkyl, is cyclopropyl, cyclobutyl, cyclopentyl, cyclohexyl, cycloheptyl and cyclooctyl. Preference is given to cyclopentyl and cyclohexyl, especially cyclopropyl.

Halogen-substituted carbon-containing groups and compounds, such as haloalkyl and haloalkoxy, may be partly halogenated or perhalogenated, the halogen substituents in the case of multiple halogenation being identical or different. Examples of haloalkyl, as a group per se and also as a structural element of other groups and compounds, such as of haloalkoxy, are methyl substituted from one to three times by fluorine, chlorine and/or bromine, such as $CHF_2$, $CF_3$ or $CH_2Cl$; ethyl substituted from one to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CH_2CH_2Cl$, $CF_2CHBr_2$, $CF_2CHClF$, $CF_2CHBrF$ or $CClFCHClF$; propyl or isopropyl substituted from one to seven times by fluorine, chlorine and/or bromine, such as $CH_2CHBrCH_2Br$, $CF_2CHFCF_3$, $CH_2CF_2CF_3$, $CF_2CF_2CF_3$, $CH(CF_3)_2$ or $CH_2CH_2CH_2Cl$; and butyl or one of its isomers substituted from one to nine times by fluorine, chlorine and/or bromine, such as $CF(CF_3)CHFCF_3$, $CF_2(CF_2)_2CF_3$ or $CH_2(CF_2)_2CF_3$.

Aryl is particularly phenyl or naphthyl; phenyl is preferred.

Heterocyclyl is a 5- to 7-membered saturated or unsaturated, preferably aromatic, ring having from one to four heteroatoms selected from the group consisting of N, O and S. Preference is given to aromatic 5- and 6-membered rings containing a nitrogen heteroatom and, if desired, a further heteroatom, preferably nitrogen, oxygen or sulfur, especially nitrogen and oxygen. Preferred heterocyclyl radicals are, for example, pyrrolyl, pyazolyl [sic], imidazolyl, 1,2,4-triazolyl, tetrazolyl, pyrazinyl, pyridyl, pyrimidinyl, pyridazinyl, oxadiazinanyl, thiazolyl, thiadiazinyl, isothiazolyl, isoxazolyl, indolyl, indazolyl, benzimidazolyl, benzothiazolyl, furanyl, tetrahydrofuranyl and thienyl.

Preferred embodiments in the context of the invention are (2) Compounds as per (1) of the formula (I) in which $R_1$ and $R_2$ independently of one another are halogen, $C_1$–$C_2$alkyl, halo-$C_1$–$C_2$alkyl, $C_1$–$C_2$alkoxy or halo-$C_1$–$C_2$alkoxy;

in particular, are independently of one another fluorine, chlorine, methyl, trifluoromethyl, methoxy or trifluoromethoxy;

especially are independently of one another fluorine, trifluoromethyl or trifluoromethoxy;

with very particular preference, in which $R_1$ and $R_2$ are trifluoromethyl;

(3) Compounds as per (1) or (2) of the formula (I) in which $R_3$ is hydrogen, OH, halogen or $C_1$–$C_6$alkoxy;

in particular is hydrogen, OH, fluorine or methoxy;

especially, is hydrogen or OH; with very particular preference, is OH;

(4) Compounds as per (1) to (3) of the formula (I) in which $R_4$ is hydrogen, chlorine, fluorine, methoxy, trifluoromethyl or trifluoromethoxy; in particular is hydrogen;

(5) Compounds as per (1) to (4) of the formula (I) in which $R_5$ is $C_1$–$C_6$alkyl, $C_3$–$C_{12}$alkenyl, $C_3$–$C_{12}$alkynyl, $C_3$–$C_8$cycloalkyl, —C(=O)—O—$R_7$, —C(=S)—O—$R_8$, —C(=Y)—Z—$R_8$, —S(=O)$_p$—$R_9$, phenyl-$C_1$–$C_6$alkyl, or phenyl-$C_1$–$C_6$alkyl substituted from one to three times independently of one another by halogen, cyano, nitro, halo-$C_1$–$C_6$alkyl or halo-$C_1$–$C_6$alkoxy;

preferably is —C(=O)—O—$R_7$, —C(=S)—O—$R_8$, —C(=Y)—Z—$R_8$, —S(=O)$_p$—$R_9$ or phenyl-$C_1$–$C_6$alkyl;

(6) Compounds as per (1) to (4) of the formula (I) in which $R_5$ is $C_3$–$C_{12}$alkynyl, especially $C_3$alkynyl;

(7) Compounds as per (1) to (4) of the formula (I) in which $R_5$ is —C(=O)—O—$R_7$ and $R_7$ is $C_1$–$C_2$alkoxy-$C_1$–$C_2$alkyl, $C_3$–$C_6$alkynyl, $C_1$–$C_2$alkyl-S(=O)$_p$—$C_1$–$C_6$alkyl, $C_3$–$C_8$cycloalkyl, phenyl, or benzyl, in particular is $C_3$–$C_6$alkynyl, especially —$CH_2$—C≡CH;

(8) Compounds as per (1) to (4) of the formula (I) in which $R_5$ is —C(=S)—O—$R_8$ and $R_8$ is $C_1$–$C_6$alkyl, $C_1$–$C_6$alkoxy-$C_1$–$C_6$alkyl, $C_2$–$C_6$alkenyl, $C_3$–$C_6$alkynyl, $C_3$–$C_8$cycloalkyl, phenyl or benzyl;

(9) Compounds as per (1) to (4) of the formula (I) in which $R_5$ is —C(=O)—Z—$R_8$, Z is sulfur, and $R_8$ is $C_1$–$C_6$alkyl, halo-$C_1$–$C_6$alkyl, $C_1$–$C_6$alkoxy-$C_1$–$C_6$alkyl, $C_1$–$C_6$alkylthio-$C_1$–$C_6$alkyl, $C_2$–$C_6$alkenyl, $C_3$–$C_6$alkynyl, $C_3$–$C_8$cycloalkyl, phenyl or benzyl;

(10) Compounds as per (1) to (4) of the formula (I) in which $R_5$ is —C(=Y)—Z—$R_8$, Z is a bond;

Y is O or S, preferably O; and $R_8$ is $C_1$–$C_6$alkyl, halo-$C_1$–$C_6$alkyl, $C_1$–$C_6$alkoxy-$C_1$–$C_6$alkyl, $C_1$–$C_6$alkylthio-$C_1$–$C_6$alkyl, $C_2$–$C_6$alkenyl, $C_3$–$C_6$alkynyl, $C_3$–$C_8$cycloalkyl, phenyl or benzyl;

(11) Compounds as per (1) to (4) of the formula (I) in which $R_5$ is —C(=Y)—Z(N$R_{10}$)—$R_8$, Y is O or S, preferably O;

$R_8$ is $C_1$–$C_6$alkyl, halo-$C_1$–$C_6$alkyl, $C_1$–$C_6$alkoxy-$C_1$–$C_6$alkyl, $C_1$–$C_6$alkylthio-$C_1$–$C_6$alkyl, $C_2$–$C_6$alkenyl, $C_3$–$C_6$alkynyl, $C_3$–$C_8$cycloalkyl, phenyl or benzyl; and $R_{10}$ is hydrogen or $C_1$–$C_6$alkyl, especially hydrogen;

(12) Compounds as per (1) to (4) of the formula (I) in which $R_5$ is —S(=O)$_p$—$R_9$;

$R_9$ is $C_1$–$C_6$alkyl, halo-$C_1$–$C_6$alkyl, $C_3$–$C_8$cycloalkyl or benzyl; especially $C_1$–$C_2$alkyl or halo-$C_1$–$C_2$alkyl; and p is 2;

(13) Compounds as per (1) to (4) of the formula (I) in which $R_5$ is phenyl or phenyl which is substituted once or twice independently of one another by halogen, trifluoromethyl or trifluoromethoxy;

(14) Compounds as per (1) to (13) of the formula (I) in which

R$_6$ is hydrogen, C$_1$–C$_6$alkyl, C$_3$–C$_8$cycloalkyl or benzyl; especially C$_1$–C$_6$alkyl, or hydrogen; very particularly hydrogen;

(15) Compounds as per 1) to 14) of the formula (I) in which q is 1;

(16) Compounds as per 1) to 3) of the formula (I) in which

R$_5$ and R$_6$ jointly, together with the nitrogen atom to which they are attached, form a heterocyclic ring which is unsubstituted or substituted.

Particular preference is given in the context of the invention to the compounds of the formula (I) that are listed in the Tables.

The invention further provides a process for preparing the compounds of the formula (I), or a salt thereof, which comprises (a) for preparing a compound of the formula (I) in which q is 0, treating a compound of the formula

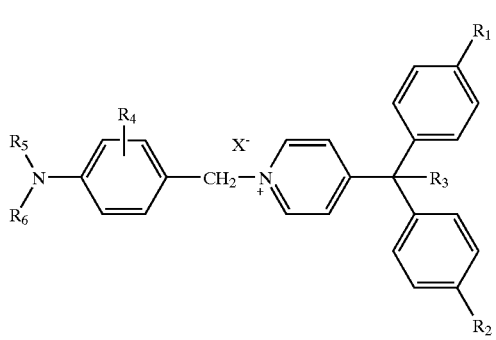

(II)

in which R$_1$, R$_2$, R$_3$, R$_4$, R$_5$ and R$_6$ are as defined above for formula (I) and X is a counterion such as halogen, sulfate or phosphate with a reducing agent such as NaBH$_4$, for example, in the absence or presence of a solvent which is inert under the chosen reaction conditions, and, if desired, (b) for preparing a compound of the formula (I) in which q is 1, reacting the resultant compound of the formula (I) in which q is 0, where appropriate, with an oxidizing agent, especially H$_2$O$_2$.

The invention additionally provides a process for preparing a compound of the formula (II) or a salt thereof, which comprises (c) if R$_1$ and R$_2$ are identical, reacting a compound of the formula

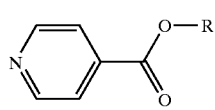

(III)

which is known or may be prepared by conventional processes and in which R is C$_1$–C$_{12}$alkyl or benzyl with two moles of a compound of the formula

(IV)

which is known or may be prepared by conventional processes and in which R$_1$ is as defined above for formula (I) in the presence of magnesium or n-butyllithium; and (d) reacting the resultant compound of the formula

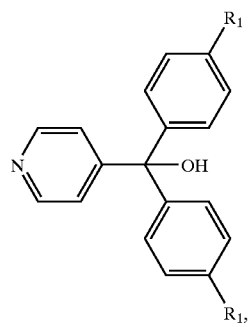

(V)

in which R$_1$ is as defined above for formula (I), and which is known or may be prepared by conventional processes, with a compound of the formula

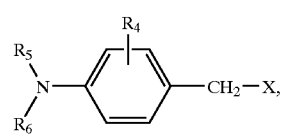

(VI)

in which R$_4$, R$_5$ and R$_6$ are as defined above for formula (I) and X is a leaving group, preferably chlorine or bromine.

The invention additionally provides a process for preparing compounds of the formula (I) as defined above and in which q is 0, or a salt thereof, which comprises (e) for preparing a compound of the formula (I) in which R$_1$ and R$_2$ are identical or different, R$_3$ is OH and q is 0, reacting a compound of the formula (IV) with isonicotinonitrile in the presence of magnesium or n-butyllithium and reacting the compound obtained following acidic hydrolysis, of the formula

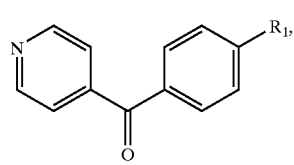

(VII)

in which R$_1$ is as defined above for the formula (I), and which is known per se, with a compound of the formula

(VIII)

which is known or may be prepared by conventional processes, and in which R$_2$ is as defined above for formula (I), in the presence of magnesium or n-butyllithium; and further reacting the resulting compound of the formula

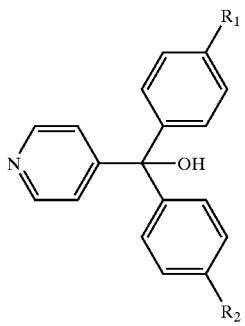

(IX)

which is known and in which $R_1$ and $R_2$ are as defined above for the formula (I) in analogy to process steps (d), (a) and, where appropriate, (b) to give a compound of the formula (I); or (f) for preparing a compound of the formula (I) in which $R_3$ is hydrogen, reacting a compound of the formula (IX) with a reducing agent such as triethylsilane, for example, in the presence of trifluoroacetic acid or trifluoromethanesulfonic acid to give a compound of the formula

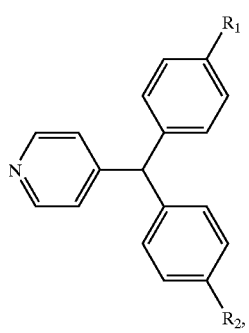

(X)

which is known per se and in which $R_1$ and $R_2$ are as defined above for the formula (I) and further reacting this compound of the formula (X) in analogy to process steps (d), (a) and, where appropriate, (b);

(g) for preparing a compound of the formula (I) in which $R_3$ is alkoxy, further reacting a compound of the formula (IX) with an alkyl halide in the presence of a strong base, such as sodium hydride, for instance, to give a compound of the formula

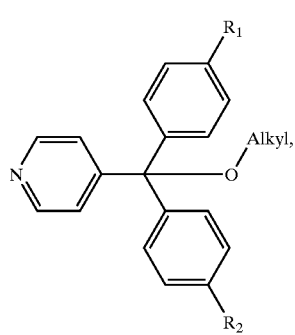

(XI)

which is known per se and in which $R_1$ and $R_2$ are as defined above for the formula (I), and further reacting this compound of the formula (XI) in analogy to process steps (d), (a) and, where appropriate, (b) to give a compound of the formula (I);

and/or, if desired, converting a compound of the formula (I) in free form or in salt form, obtainable in accordance with the process or otherwise, into another compound of the formula (I), resolving an isomer mixture obtainable in accordance with the process and isolating the desired isomer, and/or converting a free compound of the formula (I) obtainable in accordance with the process or otherwise into a salt or converting a salt of a compound of the formula (I) obtainable in accordance with the process or otherwise into the free compound of the formula (I) or into another salt.

The invention further provides a process for preparing a compound of the formula (I) as defined above, which comprises (h) in analogy to the above-described process steps (c) to (g), preparing a compound of the formula

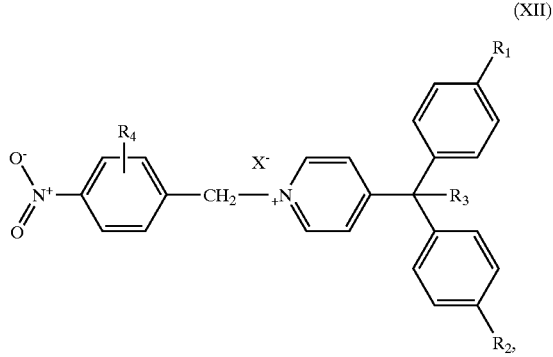

(XII)

in which $R_1$, $R_2$, $R_3$, $R_4$ and X are defined above for formula (I), and in which instead of a compound of the formula (VI) in process step (d) a compound of the formula

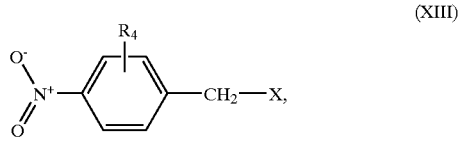

(XIII)

in which $R_4$ and X are as defined for formula (VI), and which is known or may be prepared by conventional processes, is used;

(i) reducing the resulting compound of the above formula (XII) in analogy to the above process step (a) to a compound of the formula

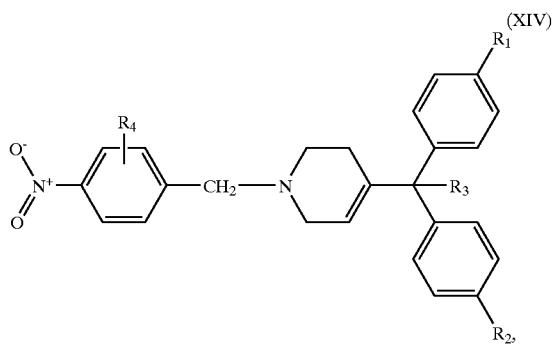

(XIV)

in which $R_1$, $R_2$, $R_3$, and $R_4$ are as defined above for formula (I);

(j) reducing the resulting compound of the formula (XIV) with hydrogen in the presence of a hydrogenation catalyst, preferably Raney nickel, to a compound of the formula

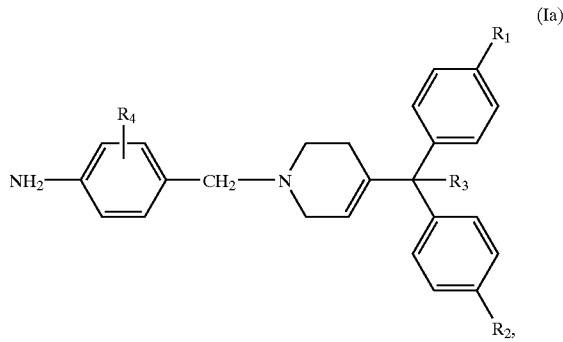

in which $R_1$, $R_2$, $R_3$, and $R_4$ are as defined above for formula (I); and (k) for preparing a compound of the formula (I) in which $R_5$ is unsubstituted or halogenated $C_1$–$C_{12}$alkyl, unsubstituted or halogenated $C_2$–$C_{12}$alkenyl, unsubstituted or halogenated $C_2$–$C_{12}$alkynyl, $C_3$–$C_8$cycloalkyl, C(=O)—O—$R_7$, C(=S)—O—$R_8$, C(=Y)—$R_8$, S(=O)$_p$—$R_9$, aryl, aryl-$C_1$–$C_6$alkyl, heterocyclyl or heterocyclyl-$C_1$–$C_6$alkyl; or is unsubstituted or substituted $C_3$–$C_8$cycloalkyl, aryl, aryl-$C_1$–$C_6$alkyl, heterocyclyl or heterocyclyl-$C_1$–$C_6$alkyl; and $R_6$ is hydrogen, and $R_7$, $R_8$, $R_9$ and p are as defined above; reacting the compound of the formula (Ia) with unsubstituted or halogenated Q-$C_1$–$C_{12}$alkyl, unsubstituted or halogenated Q-$C_2$–$C_{12}$alkenyl, unsubstituted or halogenated Q-$C_2$–$C_{12}$alkynyl, Q-$C_3$–$C_8$cycloalkyl, Q-C(=O)—O—$R_7$, Q-C(=S)—O—$R_8$, Q-C(=Y)—$R_8$, Q-S(=O)$_p$—$R_9$, Q-aryl, aryl-$C_1$–$C_6$alkyl [lacuna], Q-heterocyclyl or heterocyclyl-$C_1$–$C_6$alkyl-Q; or unsubstituted or substituted Q-$C_3$–$C_8$cycloalkyl, Q-aryl, aryl-$C_1$–$C_6$alkyl-Q, Q-heterocyclyl or heterocyclyl-$C_1$–$C_6$alkyl-Q, in which Q is a leaving group, and $R_7$, $R_8$, $R_9$ and p are as defined above; or (l) for preparing a compound of the formula (I) in which $R_5$ has the definitions indicated under process variant (k) and $R_6$ is $C_1$–$C_{12}$alkyl, $C_2$–$C_{12}$alkenyl, $C_2$–$C_{12}$alkynyl, $C_3$–$C_8$cycloalkyl or benzyl, reacting a compound of the formula (I) obtained, for example, in accordance with process variant (k) with a compound of the formula Q-$C_1$–$C_{12}$alkyl, Q-$C_2$–$C_{12}$alkenyl, Q-$C_2$–$C_{12}$alkynyl, Q-$C_3$–$C_8$cycloalkyl or Q-benzyl; in which Q is a leaving group; or (m) for preparing a compound of the formula (I) in which $R_5$ is —C(=Y)—NH—$R_8$ and $R_6$ is hydrogen, and $R_8$ and Y are as defined above, reacting a compound of the above formula (Ia) with a compound of the formula (Y=)CNR$_8$; and, where appropriate (n) reacting a resulting compound of the formula (I) in which q is 0 in analogy to process step (b) to give a compound in which q is 1.

The starting materials set out above and below of the formulae (III) to (XI) and (XIII) which [lacuna] for the preparation of the compounds of the formula (I) are known or may be prepared by conventional methods. The compounds of the formulae (Ia), (II), (XII) and (XIV) are novel and are therefore likewise provided by the invention. For the substituents of the compounds (Ia), (II), (XII) and (XIV), the same preferences apply as for the compounds of the formula (I).

The reactions described above and below are conducted in a manner known per se; for example in the absence or, where appropriate, in the presence of a suitable solvent or diluent or a mixture thereof, operating where necessary with cooling, at room temperature or with heating, e.g. in a temperature range from about –80° C. to the boiling temperature of the reaction mixture, preferably from about –20° C. to about +150° C., and, where necessary, in a closed vessel, under pressure, in an inert gas atmosphere and/or under anhydrous conditions. Particularly advantageous reaction conditions may be inferred from the examples.

Above and below, references to a leaving group or counterion are to be understood as meaning all eliminable groups which are commonly suitable in chemical reactions, such as are known to the skilled worker; especially halogens such as fluorine, chlorine, bromine, iodine, —O—C(=O)—A, —O—P(=O)(W)$_2$, —O—Si($C_1$-$C_8$alkyl)$_3$, —O—($C_1$-$C_8$alkyl), —O-aryl, —O—S(=O)$_2$W, —S—P(=O)(W)$_2$, —S—P(=S)(W)$_2$, —S—S—($C_1$-$C_8$alkyl), —S—S-aryl, —S—($C_1$-$C_8$alkyl), —S-aryl, —S(=O)W, or —S(=O)$_2$W, in which W is unsubstituted or substituted $C_1$-$C_8$alkyl, $C_2$-$C_8$alkenyl, $C_2$-$C_8$alkynyl, unsubstituted or substituted aryl, unsubstituted or substituted benzyl, $C_1$-$C_8$alkoxy or di-($C_1$-$C_8$alkyl)amine, in which the alkyl groups are independent of one another; $NO_3$, $NO_2$, or sulfate, sulfite, phosphate, phosphite, carboxylate, imino ester, $N_2$ or carbamate; or, in the case of counterions, the anions of the said groups. A particularly preferred leaving group is chlorine or bromine, especially chlorine; or, respectively, chloride or bromide, especially chloride.

Examples of oxidizing agents used are inorganic peroxides, such as sodium perborate, potassium permanganate or hydrogen peroxide; or organic peracids, such as perbenzoic acid or peracetic acid, or mixtures of organic acids and hydrogen peroxide, such as acetic acid/hydrogen peroxide, for example.

The reaction of process (a) and (i) takes place preferably in alcohols, such as methanol or ethanol, for example, in a temperature range from 0° C. to +50° C., preferably at room temperature. A preferred reducing agent is sodium borohydride.

In process variants (b) and (n) it is preferred to use alcohols as solvents, such as methanol or ethanol, for example. It is preferred to operate at from room temperature to 50° C.; suitable oxidizing agents are those mentioned above, especially $H_2O_2$ or peracides, especially $H_2O_2$.

In the case of process variants (c) and (e) preference is given to using dialkyl ethers or tetrahydrofuran as solvents; the process is operated in a temperature range from –70° C. to room temperature, and the metallating agent used is magnesium or n-butyllithium.

In the case of process variant (d), inert solvents such as benzene, toluene, xylenes, acetonitrile, propionitrile, ethyl acetate, propyl acetate, butyl acetate, acetone, diethyl ketone, methyl ethyl ketone, methyl isobutyl ketone, nitromethane or nitroethane, for example, are used. The temperature range is situated from room temperature to the reflux of the corresponding solvent, the reflux temperature being preferred.

In the case of process variant (f), the reducing agent used is preferably triethylsilane in the presence of an acid, such as trifluoroacetic acid or trifluoromethanesulfonic acid, for example.

In the case of process variant (g), particularly suitable solvents are dimethylformamide or tetrahydrofuran, preferably dimethylformamide; a preferred base is sodium hydride.

Process variant (j) is conducted preferably in an ether such as tetrahydrofuran, for instance, and at room temperature.

In the case of process variants (k), (l) and (m), preferred solvents used are apolar hydrocarbons, halogenated hydrocarbons such as chloroform or dichloromethane, for instance, or ethers such as tetrahydrofuran or dioxane; and preferred bases used are tertiary amines such as triethylamine, for instance; or heterocyclic aromatics, preferably pyridine. Operation at room temperature is preferred.

Compounds of the formula (I) obtainable in accordance with the process or otherwise may be converted conventionally into other compounds of the formula (I) by replacing one or more substituents of the starting compound of the formula (I) in conventional manner by one or more other substituents in accordance with the invention.

Depending on the choice of particular suitable reaction conditions and starting materials, it is possible in one reaction step to replace only one substituent by another substituent in accordance with the invention, or in the same reaction step it is possible to replace two or more substituents by other substituents in accordance with the invention.

Salts of compound [sic] of the formula (I) may be prepared conventionally. For example, salts of compounds of the formula (I) with bases are obtained by treating the free compounds with an appropriate base or an appropriate ion exchange reagent.

Salts of compounds of the formula (I) may be converted conventionally into the free compounds of the formula (I) by means, for example, of treatment with a suitable acid or a suitable ion exchange reagent.

Salts of compounds of the formula (I) may be transformed conventionally into other salts of a compound of the formula (I).

The compounds of the formula (I) in free form or in salt form may be present in the form of one of the possible isomers or as a mixture thereof: for example, depending on the number, absolute and relative configuration of asymmetric carbon atoms in the molecule and/or on the configuration of nonaromatic double bonds in the molecule, as pure isomers, such as enantiomers and/or diastereomers, or as isomer mixtures, such as enantiomer mixtures, e.g. racemates, diastereomer mixtures or racemate mixtures. The invention relates both to the pure isomers and to all possible isomer mixtures and should be understood accordingly in each case above and below, even if stereochemical details are not mentioned specifically in each case.

Diastereomer mixtures, racemate mixtures and mixtures of double-bond isomers of compounds of the formula (I) in free form or in salt form, obtainable in accordance with the process—depending on the choice of starting materials and procedures—or otherwise may be resolved into the pure diastereomers or racemates in a known way on the basis of the physicochemical differences of the constituents, for example by fractional crystallization, distillation and/or chromatography.

Enantiomer mixtures obtainable accordingly, such as racemates, may be separated into the optical isomers by known methods, for example by recrystallization from an optically active solvent, by chromatography on chiral adsorbents, for example high-performance liquid chromatography (HPLC) on acetylcellulose, with the aid of suitable microorganisms, by cleavage with specific immobilized enzymes, via the formation of inclusion compounds, for example using chiral crown ethers, in which case only one enantiomer is complexed, or by conversion into diastereomeric salts and separation of the diastereomer mixture obtained in this way, for example by fractional crystallization on the basis of their different solubilities into the diastereomers, from which the desired enantiomer may be liberated by the action of appropriate agents.

Apart from by resolving corresponding isomer mixtures, pure diastereomers and enantiomers, respectively, may also be obtained in accordance with the invention by commonly known methods of diastereoselective or enantioselective synthesis, for example by performing the process of the invention with starting materials of appropriate stereochemistry.

The biologically more active isomer, for example enantiomer or diastereomer, or isomer mixture, for example enantiomer mixture or diastereomer mixture, is advantageously isolated and/or synthesized, where the individual components possess different biological activity.

The compounds of formula (I) in free form or in salt form may also be obtained in the form of their hydrates and/or may include other solvents, examples being those used, where appropriate, for the crystallization of compounds present in solid form.

The invention relates to all those embodiments of the process which start from a compound obtainable at any stage of the process as a starting product or intermediate and in which all or some of the absent steps are carried out or a starting material is used in the form of a derivative and/or salt and/or its racemates and/or enantiomers or in particular is formed under the reaction conditions.

In the process of the present invention, it is preferred to use those starting materials and intermediates, in each case in free form or in salt form, which lead to the compound of the formula (I) described at the outset as being particularly valuable, and, respectively, the salts thereof.

The invention relates in particular to the preparation process described in Example H1.

The compounds of the invention of the formula (I) are preventively and/or curatively valuable active ingredients having a very favourable biocidal spectrum in the field of pest control, even at low use concentrations, while being favourably tolerated by homeotherms, fish and plants. The active ingredients of the invention are active against all or individual development stages of normally sensitive, but also resistant, animal pests, such as insects or representatives of the order Acarina. The insecticidal or acaricidal action of the active ingredients of the invention may be manifested directly i.e. in the death of the pests, which occurs directly or only after a certain time, for example during ecdysis, or indirectly, for example in reduced oviposition and/or hatching rate, the good action corresponding to a kill rate (mortality) of at least 50 to 60%.

Examples of the animal pests mentioned include those which are set out in the European Patent Application EP-A-736 252 page 5 line 55 to page 6, line 55. The pests mentioned therein are therefore incorporated by reference in the present invention's subject-matter. The active ingredients of the invention are especially suitable for the control of *Boophilus microplus, Nilaparvata lugens* and *Tetranychus urticae*, preferably for the control of these pests in vegetable, fruit and rice cultures.

The active ingredients of the invention may be used in particular to control pests of the type mentioned which occur on plants, especially on useful plants and ornamentals, in agriculture, in horticulture and in forestry, or on parts of such plants, such as fruits, flowers, foliage, stems, tubers or roots, such control meaning containment or destruction, with the protection against these pests in some cases also extending to plant parts which are formed at a later point in time.

Particularly suitable target cultures include cereals, such as wheat, rye, barley, oats, rice, maize or sorghum; beet, such as sugar beet or fooder beet; fruit, for example pome fruit, stone fruit and soft fruit, such as apples, pears, plums, peaches, almonds, cherries or berries, for example strawberries, raspberries or blackberries; pulses, such as beans, lentils, peas or soya beans; oil crops, such as oil seed rape, mustard, poppies, olives, sunflowers, coconut, caster-oil plant, cacao or peanuts; cucurbits, such as squash, cucumbers or melons; fibre crops, such as cotton, flax, hemp or jute; citrus fruits, such as oranges, lemons, grapefruit or tangerines; vegetables, such as spinach, lettuce, asparagus, cabbages, carrots, onions, tomatoes, potatoes or capsicum; Lauraceae, such as avocado, cinnamon or camphor; and also tobacco, nuts, coffee, egg plants, sugar cane, tea, pepper, grapevines, hops, Musaceae, latex plants and ornamentals.

Further fields of use of the active ingredients of the invention are in the protection of stored products and stores and of material and also in the hygiene sector, in particular the protection of domestic animals and livestock against pests of the type mentioned.

The invention therefore also relates to pesticide compositions (pesticides), such as—to be chosen in accordance with the intended objectives and prevailing circumstances—emulsifiable concentrates, suspension concentrates, directly sprayable or dilutable solutions, spreadable pastes, dilute emulsions, sprayable powders, soluble powders, dispersible powders, wettable powders, dusts, granules or encapsulations in polymeric materials, which comprise at least one of the active ingredients of the invention.

In these compositions the active ingredient is used in straight form, a solid active ingredient for example in a specific particle size, or, preferably, together with at least one of the auxiliaries common in the art of formulation, such as extenders, for example solvents or solid carriers, or such as surface-active compounds (surfactants).

Examples of formulating auxiliaries used include solid carriers, solvents, stabilizers, slow release auxiliaries, colorants, and, where appropriate, surface-active substances (surfactants). Suitable carriers and auxiliaries here include all of the substances commonly used in plant protection compositions, especially slug and snail control compositions (molluscicides). Suitable auxiliaries, such as solvents, solid carriers, surface-active compounds, nonionic surfactants, cationic surfactants, anionic surfactants and further auxiliaries, in the compositions used in accordance with the invention are for example the same as those described in EP-A-736 252 they are incorporated by reference in the present invention's subject-matter.

The compositions generally include from 0.1 to 99%, in particular from 0.1 to 95%, of active ingredient and from 1 to 99.9%, in particular from 5 to 99.9%, of at least one solid or liquid auxiliary, it being possible in general for from 0 to 25%, in particular from 0.1 to 20%, of the compositions to comprise surfactants (% denotes in each case percent by weight). While concentrated compositions tend to be the preferred commercial product, the end user generally uses dilute compositions with substantially lower active ingredient concentrations. Preferred compositions are made up in particular as follows (%=percent by weight):

| Emulsifiable concentrates: | |
| --- | --- |
| Active ingredient: | 1 to 95%, preferably 5 to 20% |
| Surfactant: | 1 to 30%, preferably 10 to 20% |
| Solvent: | 5 to 98%, preferably 70 to 85% |
| Dusts: | |
| Active ingredient: | 0.1 to 10%, preferably 0.1 to 1% |
| Solid carrier: | 99.9 to 90%, preferably 99.9 to 99% |
| Suspension concentrates: | |
| Active ingredient: | 5 to 75%, preferably 10 to 50% |
| Water: | 94 to 24%, preferably 88 to 30% |
| Surfactant: | 1 to 40%, preferably 2 to 30% |
| Wettable powders: | |
| Active ingredient: | 0.5 to 90%, preferably 1 to 80% |
| Surfactant: | 0.5 to 20%, preferably 1 to 15% |
| Solid carrier: | 5 to 99%, preferably 15 to 98% |
| Granules: | |
| Active ingredient: | 0.5 to 30%, preferably 3 to 15% |
| Solid carrier: | 99.5 to 70%, preferably 97 to 85% |

The action of the compositions of the invention may be substantially broadened and adapted to prevailing circumstances through the addition of other active insecticidal ingredients. Suitable active ingredient additions include, for example, representatives from the following classes of active ingredient: organophosphorus compounds, nitrophenols and derivatives, formamidines, acylureas, carbamates, pyrethroids, nitroenamines and derivatives, pyrroles, thioureas and derivatives, chlorinated hydrocarbons, and *Bacillus thuringiensis* preparations. The compositions of the invention may also comprise further solid or liquid auxiliaries, such as stabilizers, for example unepoxidized or epoxidized vegetable oils (e.g. epoxidized coconut oil, rapeseed oil or soya bean oil), defoamers, for example silicone oil, preservatives, viscosity regulators, binders and/or tackifiers, and also fertilizers or other active ingredients for achieving specific effects, examples being acaricides, bactericides, fungicides, nematocides, molluscicides or selective herbicides.

The compositions of the invention are prepared in a known way, in the absence of auxiliaries for example by grinding, sieving and/or compressing a solid active ingredient or mixture of active ingredients, for example to a particular particle size, and in the presence of at least one auxiliary for example by intimate mixing and/or grinding of the active ingredient or mixture of active ingredients with the auxiliary or auxiliaries. These processes for preparing the compositions of the invention and the use of the compounds I to prepare these compositions are likewise provided by the invention.

The application techniques for the compositions, i.e. the methods of controlling pests of the abovementioned type, such as spraying, fogging, dusting, brushing, dressing, scattering or pouring, which are to be chosen in accordance with the desired objectives and prevailing circumstances, and the use of the compositions for controlling pests of the abovementioned type, are also provided by the invention. Typical use concentrations are between 0.1 and 1000 ppm, preferably between 0.1 and 500 ppm, of active ingredient. The application rates per hectare are generally from 1 to 2000 g of active ingredient per hectare, in particular from 10 to 1000 g/ha, preferably from 20 to 600 g/ha.

A preferred application technique in the field of crop protection is that of application to the foliage of the plants (foliar application), the frequency and rate of application being guided by the intensity of infestation of the pest in question. However, the active ingredient may also pass into the plants through the root system (systemic action), by the locus of the plants being drenched with a liquid composition or the active ingredient in solid form being incorporated into the locus of the plants, for example into the soil, in the form for example of granules (soil application). In the case of paddy rice cultures, such granules may be added to the flooded paddy field.

The compositions of the invention are also suitable for protecting plant propagation material, including genetically modified propagation material, for example seed, such as fruits, tubers or kernels, or plant cuttings, against animal pests. The propagation material may be treated with the composition prior to planting; seed, for example, may be dressed before sowing. The active ingredients of the invention may also be applied to seed kernels (coating) by either drenching the kernels in a liquid composition or coating them with a solid composition. The composition may also be applied to the site of application when the propagation material is being applied, for example to the seed furrow at the time of sowing. These treatment methods for plant propagation material, and the plant propagation material thus treated, are further provided by the invention.

The examples which follow serve to illustrate the invention. They do not restrict the invention. Temperatures are stated in degrees Celsius, proportions of solvents in volume fractions.

PREPARATION EXAMPLES

Example H1

Preparation of the Compound of the Formula

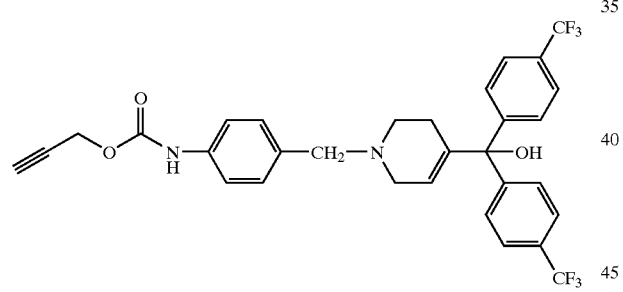

H1a) Preparation of the Compound of the Formula

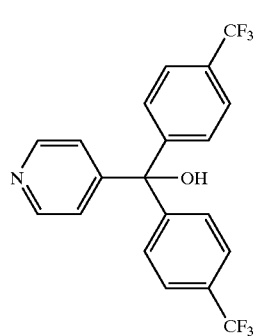

(A)

A solution of 100 g of 4-bromobenzotrifluoride in 600 ml of tetrahydrofuran is admixed dropwise at −60° C. with 278 ml of n-butyllithium (1.6 molar n-hexane solution) and the reaction temperature is allowed to rise to −40° C. Then at −65° C. 20.2 ml of ethyl isonicotinate are added dropwise over the course of one hour followed by stirring for a further hour at 0° C. The reaction mixture is then hydrolysed with 300 ml of acetic acid (10%), the water phase is separated off and the organic phase is washed with sodium chloride solution, dried over sodium sulfate and concentrated under reduced pressure. The residue is filtered over silica gel (eluent: tert-butyl methyl ether/hexane=3:1). This gives the compound (A) having a melting point of 160–163° C.

H1b) Preparation of the Compound of the Formula

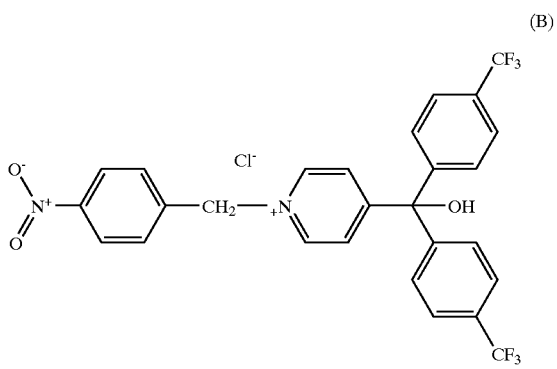

(B)

15.9 g of the compound (A) and 7.2 g of 4-nitrobenzyl chloride are stirred in 200 ml of nitromethane at 110° C. for 48 hours. The reaction mixture is then concentrated under reduced pressure and the residue is crystallized from dichloromethane/tert-butyl methylether: beige crystals. This gives the compound (B) having a melting point of 202–204° C.

H1c): Preparation of the Compound of the Formula

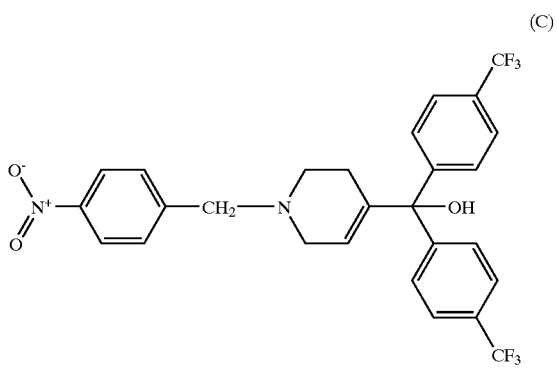

(C)

19.1 g of the compound (B) in 400 ml of methanol are admixed in portions with 1.91 g of sodium borohydride and the mixture is stirred for 1 hour. Following the addition of 5 ml of acetone, the reaction mixture is concentrated under reduced pressure, the residue is stirred with tert-butyl methyl ether/water and the water phase is separated off. The organic phase is washed with sodium chloride, dried (sodium sulfate) and concentrated under reduced pressure. The residue is filtered over silica gel (tert-butyl methyl ether/hexane=1.1): This gives the compound (C) as a resin.

H1d) Preparation of the Compound of the Formula

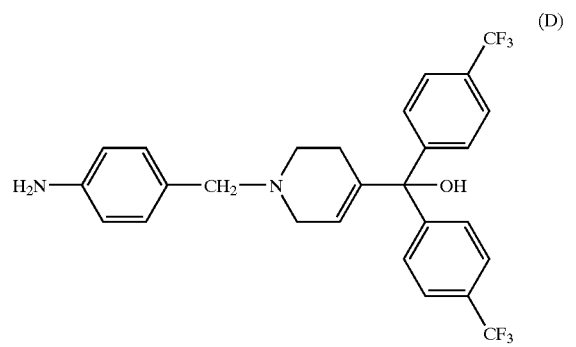
(D)

A solution of 15 g of compound (C) in 150 ml of tetrahydrofuran is stirred in the presence of 7.5 g of Raney nickel in a hydrogen atmosphere for 18 hours at room temperature under atmospheric pressure. The catalyst is filtered off and the solvent is distilled off under reduced pressure at a maximum bath temperature of 40° C. This gives the compound (D) as a foam.

H1e) Preparation of the Title Compound 2.03 g of the compound (D) in 50 ml of dichloromethane are admixed with 0.48 ml of pyridine and 0.47 ml of propargyl chloroformate and the mixture is stirred for 2 hours. The reaction mixture is then stirred with 50 ml of dichloromethane and 50 ml of water, the water phase is separated off and the organic phase is dried over sodium sulfate and concentrated under reduced pressure. The residue is chromatographed on silica gel using dichloromethane/methanol=19:1. This gives the title compound as a foam. (Compound 1.1)

Example H2

Preparation of the Compound of the Formula

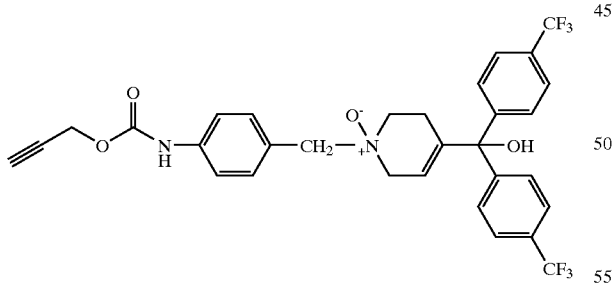

1.41 g of the compound prepared in Example H1) in 40 ml of methanol are stirred at 50° C. together with 7.4 ml of 30% hydrogen peroxide solution for 24 hours. Ethyl acetate is added to the reaction mixture, which is washed with water and sodium chloride solution, dried (sodium sulfate) and concentrated under reduced pressure. The product is recrystallized from dichloromethane/tert-butyl methyl ether. This gives the title compound with a melting point of 142-145° C. (decomposition). (Compound 1.2)

Example H3

Preparation of the Compound of the Formula

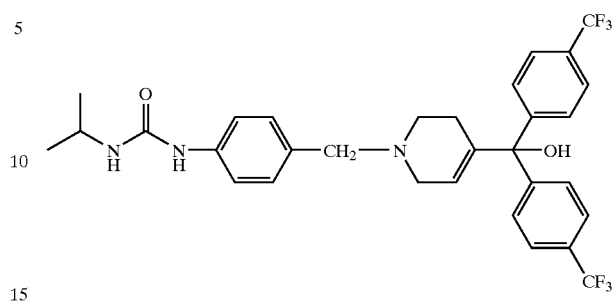

2.03 g of the compound (D) in 50 ml of dichloromethane are admixed with 0.1 ml of triethylamine and 0.43 ml of isopropyl isocyanate and the mixture is stirred for 72 hours. The reaction mixture is concentrated under reduced pressure and the residue is chromatographed on silica gel using dichloromethane/methanol=19:1. This gives the title compound as a foam (Compound 1.11).

Example H4

Preparation of the Compound of the Formula

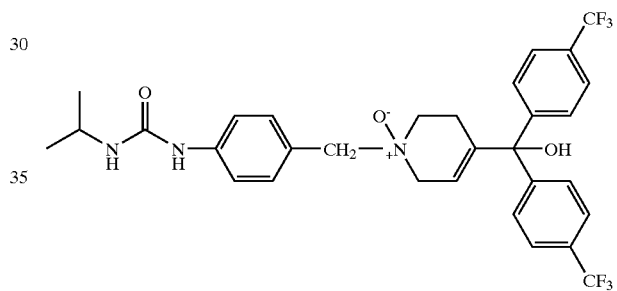

1 g of the compound prepared according to Example H3) in 30 ml of methanol is stirred at 50° C. together with 5.2 ml of 30% hydrogen peroxide solution for 24 hours. Ethyl acetate is added to the reaction mixture, which is washed with water and sodium chloride solution, dried (sodium sulfate) and concentrated under reduced pressure. From dichloromethane/hexane the title compound is thus obtained, with a melting point of 172–174° C. (decomposition, Compound 1.12).

Example H5

Preparation of the Compound of the Formula

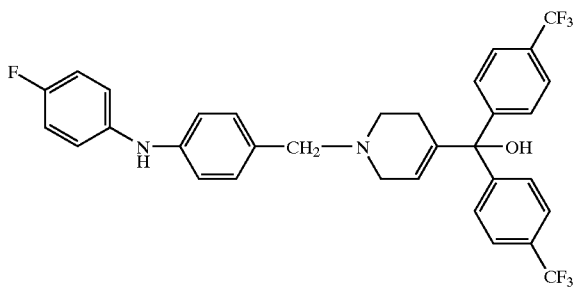

A mixture of 2.03 g of compound (D), 2.81 ml of triethylamine, 1.12 g of 4-fluorophenylboric acid and 1.09 g of copper(II)acetate in 50 ml of dichloromethane is stirred at room temperature for 96 hours. The reaction mixture is subsequently filtered and concentrated under reduced pressure and the residue is chromatographed on silica gel using ethyl acetate/hexane=3:2. This gives the title compound as a foam (Compound 1.33).

Example H6

In a manner analogous to that described above, the further compounds of the following tables may also be prepared. In the tables, Smpt. denotes the melting point in ° C., Me denotes methyl, Et ethyl, i-Prop. isopropyl, i-But. iso-butyl and c-Prop. cyclopropyl.

TABLE 1

Compounds of the formula

| Ex. No. | $R_4$ | $R_5$ | Q | Melting point |
|---|---|---|---|---|
| 1.1 | H | —COOCH$_2$—C≡CH | 0 | Foam |
| 1.2 | H | —COOCH$_2$—C≡CH | 1 | 142–145° C. (decomp.) |
| 1.3 | H | COSEthyl | 0 | Foam |
| 1.4 | H | COSEthyl | 1 | |
| 1.5 | H | CONHMethyl | 0 | |
| 1.6 | H | CONHMethyl | 1 | |
| 1.7 | H | CONHEthyl | 0 | |
| 1.8 | H | CONHEthyl | 1 | |
| 1.9 | H | CONH-n-Propyl | 0 | |
| 1.10 | H | CONH-n-Propyl | 1 | |
| 1.11 | H | CONH-i-Propyl | 0 | Foam |
| 1.12 | H | CONH-i-Propyl | 1 | 172–174° C. (decomp.) |
| 1.13 | H | CSNH-Methyl | 0 | |
| 1.14 | H | CSNH-Methyl | 1 | |
| 1.15 | H | CSNH-Ethyl | 0 | |
| 1.16 | H | CSNH-Ethyl | 1 | |
| 1.17 | H | CO-Methyl | 0 | |
| 1.18 | H | CO-Methyl | 1 | |
| 1.19 | H | CO-Ethyl | 0 | Foam |
| 1.20 | H | CO-Ethyl | 1 | 190–193° C. |
| 1.21 | H | CO—CH$_2$Cl | 0 | |
| 1.22 | H | CO—CH$_2$—OCH$_3$ | 0 | |
| 1.23 | H | CO—CH$_2$—OCH$_3$ | 1 | |
| 1.24 | H | CO—CH$_2$—SCH$_3$ | 0 | |
| 1.25 | H | CO—CH$_2$—SCH$_3$ | 1 | |
| 1.26 | H | SO$_2$CH$_3$ | 0 | |
| 1.27 | H | SO$_2$CH$_3$ | 1 | |
| 1.28 | H | SO$_2$Ethyl | 0 | |
| 1.29 | H | SO$_2$Ethyl | 1 | |
| 1.30 | H | SO$_2$CF$_3$ | 0 | |
| 1.31 | H | SO$_2$CF$_3$ | 1 | |
| 1.32 | H | Phenyl | 0 | |
| 1.33 | H | 4-F-Phenyl | 0 | Foam |
| 1.34 | H | 3-CF$_3$-Phenyl | 0 | |
| 1.35 | H | 4-CF$_3$-Phenyl | 0 | |
| 1.36 | H | 4-OCF$_3$-Phenyl | 0 | |
| 1.37 | H | 4-Cl-Phenyl | 0 | |
| 1.38 | CH$_3$ | —COOCH$_2$—C≡CH | 0 | 227–230° C. |
| 1.39 | CH$_3$ | —COOCH$_2$—C≡CH | 1 | |
| 1.40 | CH$_3$ | CONH-i-Propyl | 0' | |
| 1.41 | CH$_3$ | CONH-i-Propyl | 1 | |

TABLE 1-continued

Compounds of the formula

| Ex. No. | $R_4$ | $R_5$ | Q | Melting point |
|---|---|---|---|---|
| 1.42 | OCH$_3$ | —COOCH$_2$—C≡CH | 0 | 156–166° C. |
| 1.43 | OCH$_3$ | —COOCH$_2$—C≡CH | 1 | |
| 1.44 | OCH$_3$ | CONH-i-Propyl | 0 | |
| 1.45 | OCH$_3$ | CONH-i-Propyl | 1 | |
| 1.46 | H | CSNH-i-Propyl | 0 | |
| 1.47 | H | CSNH-i-Propyl | 1 | |

TABLE 2

Compounds of the formula

| Ex. No. | $R_4$ | $R_5$ | Q | Melting point |
|---|---|---|---|---|
| 2.1 | H | —COOCH$_2$—C≡CH | 0 | |
| 2.2 | H | —COOCH$_2$—C≡CH | 1 | |
| 2.3 | H | COSEthyl | 0 | |
| 2.4 | H | COSEthyl | 1 | |
| 2.5 | H | CONHMethyl | 0 | |
| 2.6 | H | CONHMethyl | 1 | |
| 2.7 | H | CONHEthyl | 0 | |
| 2.8 | H | CONHEthyl | 1 | |
| 2.9 | H | CONH-n-Propyl | 0 | |
| 2.10 | H | CONH-n-Propyl | 1 | |
| 2.11 | H | CONH-i-Propyl | 0 | |
| 2.12 | H | CONH-i-Propyl | 1 | |
| 2.13 | H | CSNH-Methyl | 0 | |
| 2.14 | H | CSNH-Methyl | 1 | |
| 2.15 | H | CSNH-Ethyl | 0 | |
| 2.16 | H | CSNH-Ethyl | 1 | |
| 2.17 | H | CO-Methyl | 0 | |
| 2.18 | H | CO-Methyl | 1 | |
| 2.19 | H | CO-Ethyl | 0 | |
| 2.20 | H | CO-Ethyl | 1 | |
| 2.21 | H | CO—CH$_2$Cl | 0 | |
| 2.22 | H | CO—CH$_2$—OCH$_3$ | 0 | |
| 2.23 | H | CO—CH$_2$—OCH$_3$ | 1 | |
| 2.24 | H | CO—CH$_2$—SCH$_3$ | 0 | |
| 2.25 | H | CO—CH$_2$—SCH$_3$ | 1 | |
| 2.26 | H | SO$_2$CH$_3$ | 0 | |
| 2.27 | H | SO$_2$CH$_3$ | 1 | |
| 2.28 | H | SO$_2$Ethyl | 0 | |
| 2.29 | H | SO$_2$Ethyl | 1 | |
| 2.30 | H | SO$_2$CF$_3$ | 0 | |

TABLE 2-continued

Compounds of the formula

[Structure: substituted aniline with CH2-N piperidine bearing two 4-OCF3-phenyl groups and OH, with R4, R5, (O)q]

| Ex. No. | R4 | R5 | Q | Melting point |
|---|---|---|---|---|
| 2.31 | H | SO$_2$CF$_3$ | 1 | |
| 2.32 | H | Phenyl | 0 | |
| 2.33 | H | 4-F-Phenyl | 0 | |
| 2.34 | H | 3-CF$_3$-Phenyl | 0 | |
| 2.35 | H | 4-CF$_3$-Phenyl | 0 | |
| 2.36 | H | 4-OCF$_3$-Phenyl | 0 | |
| 2.37 | H | 4-Cl-Phenyl | 0 | |
| 2.38 | CH$_3$ | —COOCH$_2$—C≡CH | 0 | |
| 2.39 | CH$_3$ | —COOCH$_2$—C≡CH | 1 | |
| 2.40 | CH$_3$ | CONH-i-Propyl | 0' | |
| 2.41 | CH$_3$ | CONH-i-Propyl | 1 | |
| 2.42 | OCH$_3$ | —COOCH$_2$—C≡CH | 0 | |
| 2.43 | OCH$_3$ | —COOCH$_2$—C≡CH | 1 | |
| 2.44 | OCH$_3$ | CONH-i-Propyl | 0 | |
| 2.45 | OCH$_3$ | CONH-i-Propyl | 1 | |
| 2.46 | H | CSNH-i-Propyl | 0 | |
| 2.47 | H | CSNH-i-Propyl | 1 | |

TABLE A

Compounds of the formula

[Structure (Ib): substituted aniline-CH2-N-piperidine with R3 and two phenyl groups bearing R1 and R2]

and of the formula

[Structure (Ic): N-oxide version]

| No. | R4 | R5 | R6 |
|---|---|---|---|
| A.1 | H | —COOCH$_2$—C≡CH | H |
| A.2 | H | —COOCH$_2$—C≡CH | CH$_3$ |
| A.3 | H | COSEthyl | H |
| A.4 | H | COSEthyl | CH$_3$ |
| A.5 | H | CONHMethyl | H |
| A.6 | H | CONHMethyl | CH$_3$ |
| A.7 | H | CONHEthyl | H |
| A.8 | H | CONHEthyl | CH$_3$ |
| A.9 | H | CONH-n-Propyl | H |
| A.10 | H | CONH-n-Propyl | CH$_3$ |
| A.11 | H | CONH-i-Propyl | H |
| A.12 | H | CONH-i-Propyl | CH$_3$ |
| A.13 | H | CSNH-Methyl | H |
| A.14 | H | CSNH-Methyl | CH$_3$ |
| A.15 | H | CSNH-Ethyl | H |
| A.16 | H | CSNH-Ethyl | CH$_3$ |
| A.17 | H | CO-Methyl | H |
| A.18 | H | CO-Methyl | CH$_3$ |
| A.19 | H | CO-Ethyl | H |
| A.20 | H | CO-Ethyl | CH$_3$ |
| A.21 | H | CO—CH$_2$Cl | H |
| A.22 | H | CO—CH$_2$Cl | CH$_3$ |
| A.23 | H | CO—CH$_2$—OCH$_3$ | H |
| A.24 | H | CO—CH$_2$—OCH$_3$ | CH$_3$ |
| A.25 | H | CO—CH$_2$—SCH$_3$ | H |
| A.26 | H | CO—CH$_2$—SCH$_3$ | CH$_3$ |
| A.27 | H | SO$_2$CH$_3$ | H |
| A.28 | H | SO$_2$CH$_3$ | CH$_3$ |
| A.29 | H | SO$_2$Ethyl | H |
| A.30 | H | SO$_2$Ethyl | CH$_3$ |
| A.31 | H | SO$_2$CF$_3$ | H |
| A.32 | H | SO$_2$CF$_3$ | CH$_3$ |
| A.33 | H | Phenyl | H |
| A.34 | H | Phenyl | CH$_3$ |
| A.35 | H | 4-F-Phenyl | H |
| A.36 | H | 4-F-Phenyl | CH$_3$ |
| A.37 | H | 3-CF$_3$-Phenyl | H |
| A.38 | H | 3-CF$_3$-Phenyl | CH$_3$ |
| A.39 | H | 4-CF$_3$-Phenyl | H |
| A.40 | H | 4-CF$_3$-Phenyl | CH$_3$ |
| A.41 | H | 4-OCF$_3$-Phenyl | H |
| A.42 | H | 4-OCF$_3$-Phenyl | CH$_3$ |
| A.43 | H | 4-Cl-Phenyl | H |
| A.44 | H | 4-Cl-Phenyl | CH$_3$ |

TABLE A-continued

Compounds of the formula (Ib)

and of the formula (Ic)

| No. | R$_4$ | R$_5$ | R$_6$ |
|---|---|---|---|
| A.45 | CH3 | —COOCH$_2$—C≡CH | H |
| A.46 | CH3 | —COOCH$_2$—C≡CH | CH$_3$ |
| A.47 | CH3 | CONH-i-Propyl | H |
| A.48 | CH3 | CONH-i-Propyl | CH$_3$ |
| A.49 | OCH3 | —COOCH$_2$—C≡CH | H |
| A.50 | OCH3 | —COOCH$_2$—C≡CH | CH$_3$ |
| A.51 | OCH3 | CONH-i-Propyl | H |
| A.52 | OCH3 | CONH-i-Propyl | CH$_3$ |
| A.53 | H | CSNH-i-Propyl | H |
| A.54 | H | CSNH-i-Propyl | CH$_3$ |

Table 3: Compounds of the general formula (Ib) in which R$_1$ and R$_2$ are CF$_3$ and R$_3$ is H and the combination of the substituents R$_4$, R$_5$ and R$_6$ for one compound corresponds in each case to a line A.1 to A.54 in Table A.

Table 4: Compounds of the general formula (Ib) in which R$_1$ and R$_2$ are CF$_3$ and R$_3$ is OH and the combination of the substituents R$_4$, R$_5$ and R$_6$ for one compound corresponds in each case to a line A.1 to A.54 in Table A.

Table 5: Compounds of the general formula (Ib) in which R$_1$ and R$_2$ are CF$_3$ and R$_3$ is F and the combination of the substituents R$_4$, R$_5$ and R$_6$ for one compound corresponds in each case to a line A.1 to A.54 in Table A.

Table 6: Compounds of the general formula (Ib) in which R$_1$ and R$_2$ are CF$_3$ and R$_3$ is OCH$_3$ and the combination of the substituents R$_4$, R$_5$ and R$_6$ for one compound corresponds in each case to a line A.1 to A.54 in Table A.

Table 7: Compounds of the general formula (Ic) in which R$_1$ and R$_2$ are CF$_3$ and R$_3$ is H and the combination of the substituents R$_4$, R$_5$ and R$_6$ for one compound corresponds in each case to a line A.1 to A.54 in Table A.

Table 8: Compounds of the general formula (Ic) in which R$_1$ and R$_2$ are CF$_3$ and R$_3$ is OH and the combination of the substituents R$_4$, R$_5$ and R$_6$ for one compound corresponds in each case to a line A.1 to A.54 in Table A.

Table 9: Compounds of the general formula (Ic) in which R$_1$ and R$_2$ are CF$_3$ and R$_3$ is F and the combination of the substituents R$_4$, R$_5$ and R$_6$ for one compound corresponds in each case to a line A.1 to A.54 in Table A.

Table 10: Compounds of the general formula (Ic) in which R$_1$ and R$_2$ are CF$_3$ and R$_3$ is OCH$_3$ and the combination of the substituents R$_4$, R$_5$ and R$_6$ for one compound corresponds in each case to a line A.1 to A.54 in Table A.

Table 11: Compounds of the general formula (Ib) in which R$_1$ is CF$_3$, R$_2$ is OCF$_3$ and R$_3$ is H and the combination of the substituents R$_4$, R$_5$ and R$_6$ for one compound corresponds in each case to a line A.1 to A.54 in Table A.

Table 12: Compounds of the general formula (Ib) in which R$_1$ is CF$_3$, R$_2$ is OCF$_3$ and R$_3$ is OH and the combination of the substituents R$_4$, R$_5$ and R$_6$ for one compound corresponds in each case to a line A.1 to A.54 in Table A.

Table 13: Compounds of the general formula (Ib) in which R$_1$ is CF$_3$, R$_2$ is OCF$_3$ and R$_3$ is F and the combination of the substituents R$_4$, R$_5$ and R$_6$ for one compound corresponds in each case to a line A.1 to A.54 in Table A.

Table 14: Compounds of the general formula (Ib) in which R$_1$ is CF$_3$, R$_2$ is OCF$_3$ and R$_3$ is OCH$_3$ and the combination of the substituents R$_4$, R$_5$ and R$_6$ for one compound corresponds in each case to a line A.1 to A.54 in Table A.

Table 15: Compounds of the general formula (Ic) in which R$_1$ is CF$_3$, R$_2$ is OCF$_3$ and R$_3$ is H and the combination of the substituents R$_4$, R$_5$ and R$_6$ for one compound corresponds in each case to a line A.1 to A.54 in Table A.

Table 16: Compounds of the general formula (Ic) in which R$_1$ is CF$_3$, R$_2$ is OCF$_3$ and R$_3$ is OH and the combination of the substituents R$_4$, R$_5$ and R$_6$ for one compound corresponds in each case to a line A.1 to A.54 in Table A.

Table 17: Compounds of the general formula (Ic) in which R$_1$ is CF$_3$, R$_2$ is OCF$_3$ and R$_3$ is F and the combination of the substituents R$_4$, R$_5$ and R$_6$ for one compound corresponds in each case to a line A.1 to A.54 in Table A.

Table 18: Compounds of the general formula (Ic) in which R$_1$ is CF$_3$, R$_2$ is OCF$_3$ and R$_3$ is OCH$_3$ and the combination of the substituents R$_4$, R$_5$ and R$_6$ for one compound corresponds in each case to a line A.1 to A.54 in Table A.

Table 19: Compounds of the general formula (Ib) in which R$_1$ and R$_2$ are OCF$_3$ and R$_3$ is H and the combination of the substituents R$_4$, R$_5$ and R$_6$ for one compound corresponds in each case to a line A.1 to A.54 in Table A.

Table 20: Compounds of the general formula (Ib) in which R$_1$ and R$_2$ are OCF$_3$ and R$_3$ is OH and the combination of the substituents R$_4$, R$_5$ and R$_6$ for one compound corresponds in each case to a line A.1 to A.54 in Table A.

Table 21: Compounds of the general formula (Ib) in which R$_1$ and R$_2$ are OCF$_3$ and R$_3$ is F and the combination of the substituents R$_4$, R$_5$ and R$_6$ for one compound corresponds in each case to a line A.1 to A.54 in Table A.

Table 22: Compounds of the general formula (Ib) in which R$_1$ and R$_2$ are OCF$_3$ and R$_3$ is OCH$_3$ and the combination of the substituents R$_4$, R$_5$ and R$_6$ for one compound corresponds in each case to a line A.1 to A.54 in Table A.

Table 23: Compounds of the general formula (Ic) in which R$_1$ and R$_2$ are OCF$_3$ and R$_3$ is H and the combination of the substituents R$_4$, R$_5$ and R$_6$ for one compound corresponds in each case to a line A.1 to A.54 in Table A.

Table 24: Compounds of the general formula (Ic) in which R$_1$ and R$_2$ are OCF$_3$ and R$_3$ is OH and the combination of the substituents R$_4$, R$_5$ and R$_6$ for one compound corresponds in each case to a line A.1 to A.54 in Table A.

Table 25: Compounds of the general formula (Ic) in which R$_1$ and R$_2$ are OCF$_3$ and R$_3$ is F and the combination of the substituents $R_4$, $R_5$ and $R_6$ for one compound corresponds in each case to a line A.1 to A.54 in Table A.

Table 26: Compounds of the general formula (Ic) in which $R_1$ and $R_2$ are $OCF_3$ and $R_3$ is $OCH_3$ and the combination of the substituents $R_4$, $R_5$ and $R_6$ for one compound corresponds in each case to a line A.1 to A.54 in Table A.

Table 27: Compounds of the general formula (Ib) in which $R_1$ is $CF_3$, $R_2$ is F and $R_3$ is H and the combination of the substituents $R_4$, $R_5$ and $R_6$ for one compound corresponds in each case to a line A.1 to A.54 in Table A.

Table 28: Compounds of the general formula (Ib) in which $R_1$ is $CF_3$, $R_2$ is F and $R_3$ is OH and the combination of the substituents $R_4$, $R_5$ and $R_6$ for one compound corresponds in each case to a line A.1 to A.54 in Table A.

Table 29: Compounds of the general formula (Ib) in which $R_1$ is $CF_3$, $R_2$ is F and $R_3$ is F and the combination of the substituents $R_4$, $R_5$ and $R_6$ for one compound corresponds in each case to a line A.1 to A.54 in Table A.

Table 30: Compounds of the general formula (Ib) in which $R_1$ is $CF_3$, $R_2$ is F and $R_3$ is $OCH_3$ and the combination of the substituents $R_4$, $R_5$ and $R_6$ for one compound corresponds in each case to a line A.1 to A.54 in Table A.

Table 31: Compounds of the general formula (Ic) in which $R_1$ is $CF_3$, $R_2$ is F and $R_3$ is H and the combination of the substituents $R_4$, $R_5$ and $R_6$ for one compound corresponds in each case to a line A.1 to A.54 in Table A.

Table 32: Compounds of the general formula (Ic) in which $R_1$ is $CF_3$, $R_2$ is F and $R_3$ is OH and the combination of the substituents $R_4$, $R_5$ and $R_6$ for one compound corresponds in each case to a line A.1 to A.54 in Table A.

Table 33: Compounds of the general formula (Ic) in which $R_1$ is $CF_3$, $R_2$ is F and $R_3$ is F and the combination of the substituents $R_4$, $R_5$ and $R_6$ for one compound corresponds in each case to a line A.1 to A.54 in Table A.

Table 34: Compounds of the general formula (Ic) in which $R_1$ is $CF_3$, $R_2$ is F and $R_3$ is $OCH_3$ and the combination of the substituents $R_4$, $R_5$ and $R_6$ for one compound corresponds in each case to a line A.1 to A.54 in Table A.

Table 35: Compounds of the general formula (Ib) in which $R_1$ and $R_2$ are $SCF_3$ and $R_3$ is H and the combination of the substituents $R_4$, $R_5$ and $R_6$ for one compound corresponds in each case to a line A.1 to A.54 in Table A.

Table 36: Compounds of the general formula (Ib) in which $R_1$ and $R_2$ are $SCF_3$ and $R_3$ is OH and the combination of the substituents $R_4$, $R_5$ and $R_6$ for one compound corresponds in each case to a line A.1 to A.54 in Table A.

Table 37: Compounds of the general formula (Ib) in which $R_1$ and $R_2$ are $SCF_3$ and $R_3$ is F and the combination of the substituents $R_4$, $R_5$ and $R_6$ for one compound corresponds in each case to a line A.1 to A.54 in Table A.

Table 38: Compounds of the general formula (Ib) in which $R_1$ and $R_2$ are $SCF_3$ and $R_3$ is $OCH_3$ and the combination of the substituents $R_4$, $R_5$ and $R_6$ for one compound corresponds in each case to a line A.1 to A.54 in Table A.

Table 39: Compounds of the general formula (Ic) in which $R_1$ and $R_2$ are $SCF_3$ and $R_3$ is H and the combination of the substituents $R_4$, $R_5$ and $R_6$ for one compound corresponds in each case to a line A.1 to A.54 in Table A.

Table 40: Compounds of the general formula (Ic) in which $R_1$ and $R_2$ are $SCF_3$ and $R_3$ is OH and the combination of the substituents $R_4$, $R_5$ and $R_6$ for one compound corresponds in each case to a line A.1 to A.54 in Table A.

Table 41: Compounds of the general formula (Ic) in which $R_1$ and $R_2$ are $SCF_3$ and $R_3$ is F and the combination of the substituents $R_4$, $R_5$ and $R_6$ for one compound corresponds in each case to a line A.1 to A.54 in Table A.

Table 42: Compounds of the general formula (Ic) in which $R_1$ and $R_2$ are $SCF_3$ and $R_3$ is $OCH_3$ and the combination of the substituents $R_4$, $R_5$ and $R_6$ for one compound corresponds in each case to a line A.1 to A.54 in Table A.

Formulation Examples (%=Percent by Weight)

| Example F1: Emulsion concentrates | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol EO) | 5% | — | — |
| Tributylphenol polyethylene glycol ether (30 mol EO) | — | 12% | 4% |
| Cyclohexanone | — | 15% | 20% |
| Xylene mixture | 65% | 25% | 20% |

Mixing of finely ground active ingredient and additives gives an emulsion concentrate which provides emulsions of desired concentration by dilution with water.

| Example F2: Solutions | a) | b) | c) | d) |
|---|---|---|---|---|
| Active ingredient | 80% | 10% | 5% | 95% |
| Ethylene glycol monomethyl ether | 20% | — | — | — |
| Polyethylene glycol (MW 400) | — | 70% | — | — |
| N-Methylpyrrolid-2-one | — | 20% | — | — |
| Epoxidized coconut oil | — | — | 1% | 5% |
| Petroleum spirit (boiling range: 160–190°) | — | — | 94% | — |

Mixing of finely ground active ingredient and additives gives a solution suitable for application in the form of very small droplets.

| Example F3: Granules | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier material mixture and the solvent is evaporated under reduced pressure.

Biological Examples

Example B1

Action Against *Heliothis virescens* Caterpillars

Young soya bean plants are sprayed with an aqueous emulsion spray liquor containing 400 ppm of the active ingredient. After the spray coating has dried on, the soya bean plants are populated with 10 first-stage caterpillars of *Heliothis virescens* and placed in a plastic container. Evaluation takes place 6 days later. The percentage reduction in population, or the percentage reduction in feeding damage (% action), is determined by comparing the number of dead caterpillars and the feeding damage on the treated plants with those on the untreated plants.

The compounds of the tables exhibit a good action against *Heliothis virescens* in this test. In particular, compounds 1.1, 1.2, 1.38 and 1.42 display an action of more than 80%.

Example B2

Action Against *Plutella xylostella* Caterpillars

Young cabbage plants are sprayed with an aqueous emulsion spray liquor containing 400 ppm of the active ingredient. After the spray coating has dried on, the cabbage plants are populated with 10 third-stage caterpillars of *Plutella xylostella* and placed in a plastic container. Evaluation takes place 3 days later. The percentage reduction in population, or the percentage reduction in feeding damage (% action), is determined by comparing the number of dead caterpillars and the feeding damage on the treated plants with those on the untreated plants.

The compounds of the tables exhibit a good action against *Plutella xylostella* in this test. In particular, compounds 1.1, 1.2, 1.38 and 1.42 display an action of more than 80%.

Example B3

Action Against *Diabrotica balteata* Larvae

Maize seedlings are sprayed with an aqueous emulsion spray liquor containing 400 ppm of the active ingredient. After the spray coating has dried on, the maize seedlings are populated with 10 second-stage larvae of *Diabrotica balteata* and placed in a plastic container. Evaluation takes place 6 days later. The percentage reduction in population (% action) is determined by comparing the number of dead larvae on the treated plants with those on the untreated plants.

The compounds of the tables exhibit a good action against *Diabrotica balteata* in this test. In particular, compounds 1.1, 1.2, 1.38 and 1.42 display an action of more than 80%.

What is claimed is:

1. A compound of the formula

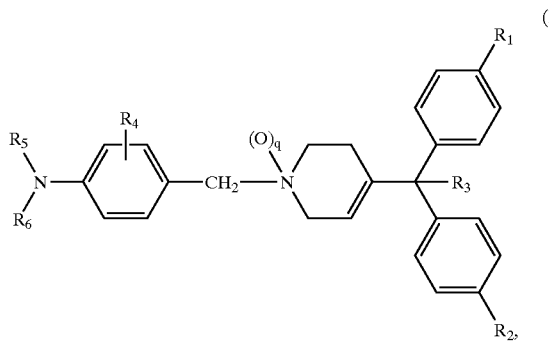

(I)

in which $R_1$ and $R_2$ independently of one another are halogen, $C_1$–$C_6$alkyl, halo-$C_1$–$C_6$alkyl, $C_1$–$C_6$alkoxy, halo-$C_1$–$C_6$alkoxy, —S(=O)$_p$—$R_9$ or SF$_5$, $R_3$ is hydrogen, OH, halogen, $C_1$–$C_6$alkoxy or —O—C(=O)—$C_1$–$C_6$alkyl, $R_4$ is hydrogen, halogen, $C_1$–$C_6$alkyl, halo-$C_1$–$C_6$alkyl, $C_1$–$C_6$alkoxy, halo-$C_1$–$C_6$alkoxy, —S(=O)$_p$—$R_9$ or —SCN;

$R_5$ and $R_6$ independently of one another are hydrogen, $C_1$–$C_{12}$alkyl, halo-$C_1$–$C_{12}$alkyl, $C_2$–$C_{12}$alkenyl, halo-$C_2$–$C_{12}$alkynyl, halo-$C_2$–$C_{12}$alkynyl, $C_3$–$C_8$cycloalkyl, —C(=O)—O—$R_7$, —C(=S)—O—$R_8$, —C(=Y)—Z—$R_8$, —S(=O)$_p$—$R_9$, aryl, or aryl-$C_1$–$C_6$alkyl; or are $C_3$–$C_8$cycloalkyl, aryl, or aryl-$C_1$–$C_6$alkyl, each substituted in the ring, depending on substitution possibilities, form one to five times independently of one another by halogen, hydroxyl, cyano, nitro, $C_1$–$C_6$alkyl, halo-$C_1$–$C_6$alkyl, $C_1$–$C_6$alkoxy or halo-$C_1$–$C_6$alkoxy;

Y is oxygen or sulfur;

Z is a bond, —NR$_{10}$— or sulfur;

$R_7$ is $C_1$–$C_6$alkoxy-$C_1$–$C_6$alkyl, $C_1$–$C_1$–$C_6$alkylthio-$C_1$–$C_6$alkyl, $C_1$–$C_6$alkylamino-$C_1$–$C_6$alkyl, $C_3$–$C_6$alkynyl, $C_1$–$C_6$alkyl-S(=O)$_p$-$C_1$–$C_6$alkyl, $C_3$–$C_6$alkynyl, $C_1$–$C_6$alkyl-S(=O)$_p$—$C_1$–$C_6$alkyl, $C_3$–$C_6$cycloalkyl, aryl, or aryl-$C_1$–$C_6$alkyl; or is $C_3$–$C_8$cycloalkyl, aryl, or aryl-$C_1$–$C_6$alkyl, each substituted in the ring, depending on substitution possibilities, from one to five times independently of one another by halogen, cyano, nitro, $C_{1–6}$alkyl, halo-$C_1$–$C_6$alkyl, $C_1$–$C_6$alkoxy or halo-$C_1$–$C_6$alkoxy;

$R_8$ is $C_1$–$C_6$alkyl, halo-$C_1$–$C_6$alkyl, $C_1$–$C_6$alkoxy-$C_1$–$C_6$alkyl, $C_1$–$C_6$alkylthio-$C_1$–$C_6$alkyl, $C_2$–$C_6$alkenyl, $C_3$–$C_6$alkynyl, $C_1$–$C_6$alkyl-S(=O)$_p$—$C_1$–$C_6$alkyl, $C_3$–$C_8$cycloalkyl, aryl, or aryl-$C_1$–$C_6$alkyl; or is $C_3$–$C_8$cycloalkyl, aryl, or aryl-$C_1$–$C_6$alkyl, each substituted in the ring, depending on substitution possibilities, from one to five times independently of one another by halogen, cyano, nitro, $C_1$–$C_6$alkyl, halo-$C_1$–$C_6$alkyl, $C_1$–$C_6$alkoxy or halo-$C_1$–$C_6$alkoxy;

$R_9$ is $C_1$–$C_6$alkyl, $C_3$–$C_8$cycloalkyl, halo-$C_1$–$C_6$alkyl or benzyl;

$R_{10}$ is hydrogen, $C_1$–$C_6$alkyl, $C_3$–$C_8$cycloalkyl, halo-$C_1$–$C_6$alkyl or benzyl;

p is 0, 1 or 2; and q is 0 or 1;

and, the E/Z isomers, E/Z isomer mixtures and/or tautomers, each in free form or in salt form.

2. A compound according to claim 1 of the formula (I) in free form.

3. A compound according to claim 1 of the formula (I) in which $R_1$ and $R_2$ independently of one another are halogen, $C_1$–$C_2$alkyl, halo-$C_1$–$C_2$alkyl, $C_1$–$C_2$alkoxy or halo-$C_1$–$C_2$alkoxy.

4. An insecticidal composition which comprises one or more compound according to claim 1 of the formula (I), in free form or in agrochemically useable salt form, as active ingredient and at least one auxiliary.

5. A method of controlling insects, which comprises applying from 0.1 to 99.9% of an insecticidal composition as described in claim 4 to the insects or their habitat.

* * * * *